US007501624B1

(12) United States Patent
Farrell et al.

(10) Patent No.: US 7,501,624 B1
(45) Date of Patent: Mar. 10, 2009

(54) SYSTEM AND METHOD FOR DETECTING CONCEALED NUCLEAR MATERIALS, RADIOLOGICAL MATERIALS AND CHEMICAL EXPLOSIVES

(75) Inventors: J. Paul Farrell, East Setauket, NY (US); Vadim Dudnikov, Alexandria, VA (US)

(73) Assignee: Brookhaven Technology Group, Inc., East Setauket, NY (US)

( * ) Notice: Subject to any disclaimer, the term of this patent is extended or adjusted under 35 U.S.C. 154(b) by 127 days.

(21) Appl. No.: 11/811,539

(22) Filed: Jun. 11, 2007

(51) Int. Cl.
*G01N 23/02* (2006.01)
(52) U.S. Cl. ............ 250/309; 250/390.04; 250/390.05; 250/306; 250/370.05; 376/159; 378/53; 378/57
(58) Field of Classification Search ................. 250/306, 250/309, 390.04, 390.1, 370.05; 376/159; 378/53, 57
See application file for complete search history.

(56) References Cited

U.S. PATENT DOCUMENTS

| | | | |
|---|---|---|---|
| 3,124,679 A | 3/1964 | Tiltman et al. | |
| 3,832,545 A | 8/1974 | Bartko | |
| 4,442,354 A | 4/1984 | Hurst et al. | |
| 4,851,687 A | 7/1989 | Ettinger | |
| 4,941,162 A | 7/1990 | Vartsky et al. | |
| 5,002,721 A | 3/1991 | Bernard et al. | |
| 5,040,200 A | 8/1991 | Ettinger et al. | |
| 5,115,459 A | 5/1992 | Bertozzi | |
| 5,159,617 A | 10/1992 | King et al. | |
| 5,247,177 A | 9/1993 | Goldberg et al. | |
| 5,251,240 A * | 10/1993 | Grodzins | 376/157 |
| 5,278,418 A * | 1/1994 | Broadhurst | 250/390.04 |
| 5,282,235 A * | 1/1994 | Schmor et al. | 378/53 |
| 5,293,414 A | 3/1994 | Ettinger et al. | |
| 5,323,004 A | 6/1994 | Ettinger et al. | |
| 5,420,905 A | 5/1995 | Bertozzi | |
| 5,606,167 A * | 2/1997 | Miller | 250/390.04 |
| 5,784,430 A | 7/1998 | Sredniawski | |
| 5,818,054 A * | 10/1998 | Randers-Pehrson et al. | 250/390.04 |
| 5,854,531 A | 12/1998 | Young et al. | |
| 6,724,852 B1 | 4/2004 | Smith et al. | |
| 7,120,226 B2 | 10/2006 | Ledoux et al. | |
| 7,151,815 B2 | 12/2006 | Ruddy et al. | |
| 7,154,102 B2 | 12/2006 | Poteet et al. | |
| 2005/0135535 A1 | 6/2005 | Wallace | |
| 2006/0140326 A1 | 6/2006 | Rowland et al. | |

OTHER PUBLICATIONS

J. Paul Farrell, et al., "A New Vacuum Insulated Tandem Accelerator for Detection of Explosives and Special Nuclear Materials," Proceedings of SPIE vol. 5769, p. 1-10 Mar. 2005.

* cited by examiner

*Primary Examiner*—Jack I Berman
*Assistant Examiner*—Michael J Logie
(74) *Attorney, Agent, or Firm*—Hoffman & Baron, LLP

(57) ABSTRACT

A system for producing beams of high energy photons and neutrons and a method to use such beams to actively interrogate and detect concealed nuclear materials, radiological materials, and chemical explosives.

9 Claims, 6 Drawing Sheets

Fig. 1

|  | Method 1 | Method 2 | Method 3 |
|---|---|---|---|
| Beam | proton | proton | deuteron |
| Energy (MeV) | 1.78 | 2.5 | 2.5 |
| DE/E (%) | 0.10% | 3.00% | 3.00% |
| Avg. Current (mA) | 5 | 5 | 5 |
| Pulse Current (mA) |  | 50 | 50 |
| Pulse Duration (ms) |  | 2 | 2 |
| Pulse Duty Cycle |  | 10% | 10% |
|  |  |  |  |
| Target material | Carbon-13 | Fluorine-19 | lithium or deuterium |
| Generated radiation | gamma | gamma | neutron |
| Energy 1 (MeV) | 9.17 | 6.129 | > 5 |
| Energy 2 (MeV) |  | 6.917 |  |
| Energy 3 (MeV) |  | 7.116 |  |
|  |  |  |  |
| Detects | Chemical explosives Shielded dirty bombs | Shielded Dirty bombs SNM | SNM |

$\sigma_1 : H^- + e \Rightarrow H + 2e;$ $\sigma_2 : H^- + H^+ \Rightarrow H + H\;;$ $\sigma_3 : H^- + H \Rightarrow H + H^-;$ $\sigma_4 : H^+ + H \Rightarrow H + H^+;$ $\sigma_5 : H^- + H \Rightarrow H + H + e$ $\sigma_6 : H^- + H_2 \Rightarrow H + H_2 + e;$ 1. ion beam centerline; 2. negative ion source; 3. high voltage terminal; 4. coaxial cylindrical electrodes;
5. pressurized voltage graded insulator; 6. vacuum vessel; 7. voltage graded column; 8. high voltage power supply.

SYSTEM AND METHOD FOR DETECTING CONCEALED NUCLEAR MATERIALS, RADIOLOGICAL MATERIALS AND CHEMICAL EXPLOSIVES

This application claims the benefit of pending U.S. patent application Ser. No. 11/414,769 filed Apr. 28, 2006, which claims the benefit of U.S. Provisional Application Ser. No. 60/676,090 filed on Apr. 28, 2005.

BACKGROUND OF THE INVENTION

This invention is concerned with the production of beams of high energy photons and/or neutrons and a method to use the beams to actively interrogate and detect concealed nuclear materials, radiological materials and chemical explosives.

In today's world, credible threat scenarios are posed by weapons-usable special nuclear materials, radiological weapons and chemical explosives. The most potentially catastrophic terrorist threat involving radioactive materials is the possibility of a self-sustained fission chain reaction detonated in an urban area. This scenario is credible and is taken very seriously by the federal authorities. Such an event could result in a significant number of deaths and massive devastation. The resulting fallout, containing highly radioactive fission and activation products, would contaminate many square miles. Such a device need only contain several kilograms to a few tens of kilograms of a fissile isotope. It could be transported in a shipping container or a small truck, and would be difficult to detect because of the relatively small amount of external radiation that it would produce, especially if shielded, before detonation.

Other credible threat scenarios include the use of ordinary radiological materials as potential weapons. A noninclusive list of potential threats includes the use of so-called "alternate nuclear materials" or the generation of "dirty" bombs, which use a combination of conventional explosives and nuclear material. Dirty bombs can be detected by passive radiation monitors if they are not shielded. If they are shielded, active interrogation using γ-rays is needed to detect the thick shield material required to hide the highly radioactive material.

Another very serious threat is that posed by bulk amounts of chemical explosives including improvised explosive devices, which could be explosives left on trains, car and truck bombs and others. These chemical explosives can be used to spread terror in the population or they can be used to produce long lasting threats to commerce by destroying bridges, tunnels and other commercially vital choke points.

The need to be able to detect special nuclear materials, alternate nuclear materials (radiological shielded "dirty" bomb) and chemical explosives leads to many requirements that are not met by current technologies (e.g., simple, unambiguous, inexpensive, rapid, detection of nuclear material, detection of chemical explosives, "dirty" bombs etc.).

Until recently, modern efforts to uniquely and unambiguously detect explosives stemmed from two unrelated occurrences: One was the downing of Pan American Flight 903 in 1989 and the other was the continuing effort to find rapid and reliable methods to detect buried explosives or land mines. In regard to airline security, the emphasis was on detection of small amounts of explosive in checked and carry-on airline baggage. The requirements for such a system were to detect quantities as small as 1 kg of nitrogen-based explosive at a rate of about one bag every 6 seconds. In addition, the cost of ownership had to be commensurate with the risk and the cost to society as a whole. In regard to land mines, the method had to be mobile over undeveloped terrain, easy to operate, technically effective and low cost.

With the events of 9/11 heralding a new level of terrorism throughout the world, the civilian need to detect explosives and now, weapons-usable special nuclear material and "dirty bombs," has increased by orders of magnitude. From a technology for detecting small amounts of explosive in luggage, the problem has changed to detection of "dirty bombs", small nukes, innovated chemical explosives and bulk amounts of explosives in trucks and cars. The risk factor has increased dramatically and so has the quantity of material and type of threat.

Electron and ion accelerators are often used to generate radiation that can penetrate materials to detect what's inside. X-rays produced by radioisotope sources and electron accelerators are used in inspection systems to inspect luggage, cargo, trucks and other containers. Neutrons produced in nuclear reactions by ion accelerators and neutron emitting radioisotopes are used for the same purposes and for detection of special nuclear materials.

Typically, a beam of charged particles, electrons or ions, is produced, accelerated to high energy and directed at a first target to produce the desired photon or neutron beam. The penetrating photon or neutron radiation produced by the reaction of the primary beam on the target passes through the closed container where it is attenuated according to the density of the material or it produces a specific response characteristic of the type of material. For example, nitrogen-based explosives resonantly absorb and re-emit gamma rays with energy of 9.17 MeV. Special nuclear materials can be made to fission and emit secondary penetrating neutron and photon radiation that can be detected and made to send an alarm. In addition, detectors can collect information on attenuation that can be used to determine density or to image the contents of the container. Resonant absorption can also be used to identify the elemental content of other materials inside. An alarm signal can be generated or an image of the contents can be produced.

It is a general requirement of an inspection process that inspection times should be as short as possible. This implies that the quantity of radiation that passes through a unit of area of the container in a unit of time should be as high as possible. This, in turn, implies that the electron or ion current and current density from the accelerator that produces the penetrating radiation be as high as possible. In an interrogation system that uses ionizing radiation, it is also important that the overall dose to the interrogated system be as low as possible. This requirement is based on the possibility that the container may include human stowaways and it is unacceptable to cause them physical harm. In addition, there may be other unknown physical, medical or biological devices or systems inside the container that would be damaged if a high dose is employed to perform the interrogation.

The requirements for short inspection times and low dose means the return signal emitted by the specific threat (explosives, special nuclear materials or shielded dirty bombs) should be highly specific of the threat material and easily distinguished for the background radiation.

The characteristics of the interrogating beam determine the specificity of the response signal. The characteristics include the type of radiation, the energy spectrum, its physical dimension and fluence, the angular divergence and the time structure of the beam. All these characteristics play important roles in determining the throughput rate, signal to noise and other information required to unambiguously characterize the hidden material inside a closed container. These characteristics of the interrogating radiation source are determined by the design and capabilities of the accelerator system that produces the primary beam and the by the design of the target where the interrogating radiation originates.

Past efforts to produce high current negative ions, accelerate them in an electrostatic tandem accelerator and transport the ions to a target have suffered serious beam current and beam emittance limitations. The problems stem from:

1. Past limitation of negative ion sources to produce low emittance, high output current negative ion beams;
2. Destruction of weakly bound negative ions due to collisions with gas in the ion source and in the low energy beam transport system before they are accelerated to high energy;
3. Voltage instability due to charge buildup on the insulating structure of the high voltage acceleration tube; and/or
4. Run away vacuum in the accelerating structure due to loss of stripper gas from the stripper canal and buildup of neutrals due to charge exchange with the ion beam.

There is therefore a need in the art for an accelerator/target system and accompanying methods capable of actively interrogating closed containers to detect the presence of special nuclear materials, radiological weapons and/or chemical explosives.

SUMMARY OF THE INVENTION

The present invention, which addresses the needs of the prior art, describes an energetic radiation source that can be used to actively interrogate containers, trucks, trains, cars, etc to determine the presence and location of chemical explosives and special nuclear materials such as uranium and plutonium. Active interrogation methods using high energy photon or neutron sources to induce fission are the only feasible option for detection of highly enriched uranium (HEU) because passive detection methods are easily compromised by even moderate amounts of shielding. The same methods of active interrogation used for HEU can be used for plutonium. For detection of chemical explosives, the same active interrogation device can be used to produce resonant photons that detect the bulk amounts of nitrogen that might be used in an ordinary bomb or to disperse a "dirty bomb" in a major city.

The radiation source is an ion accelerator based system. The system produces a penetrating beam of high energy photons or neutrons that can "see" inside sealed containers. If chemical explosives, special nuclear or shielded dirty bomb materials are present, they will emit a characteristic signal that is detected and interpreted by electronic sensors located outside the container.

The interrogating source of radiation that has the required characteristics to rapidly and unambiguously detect these three threats is comprised of four major components: a high current negative ion source, a high current tandem accelerator, appropriate targets for producing the high energy photons and neutrons, and appropriate detectors to measure the signals that result if the threat materials are present. These four major components are combined to produce the penetrating radiation that will indicate the presence of a particular threat.

BRIEF DESCRIPTION OF THE DRAWINGS

FIG. 1 is a table summarizing methods for detecting three types of dangerous materials;

DETAILED DESCRIPTION OF THE INVENTION

Figure 2:
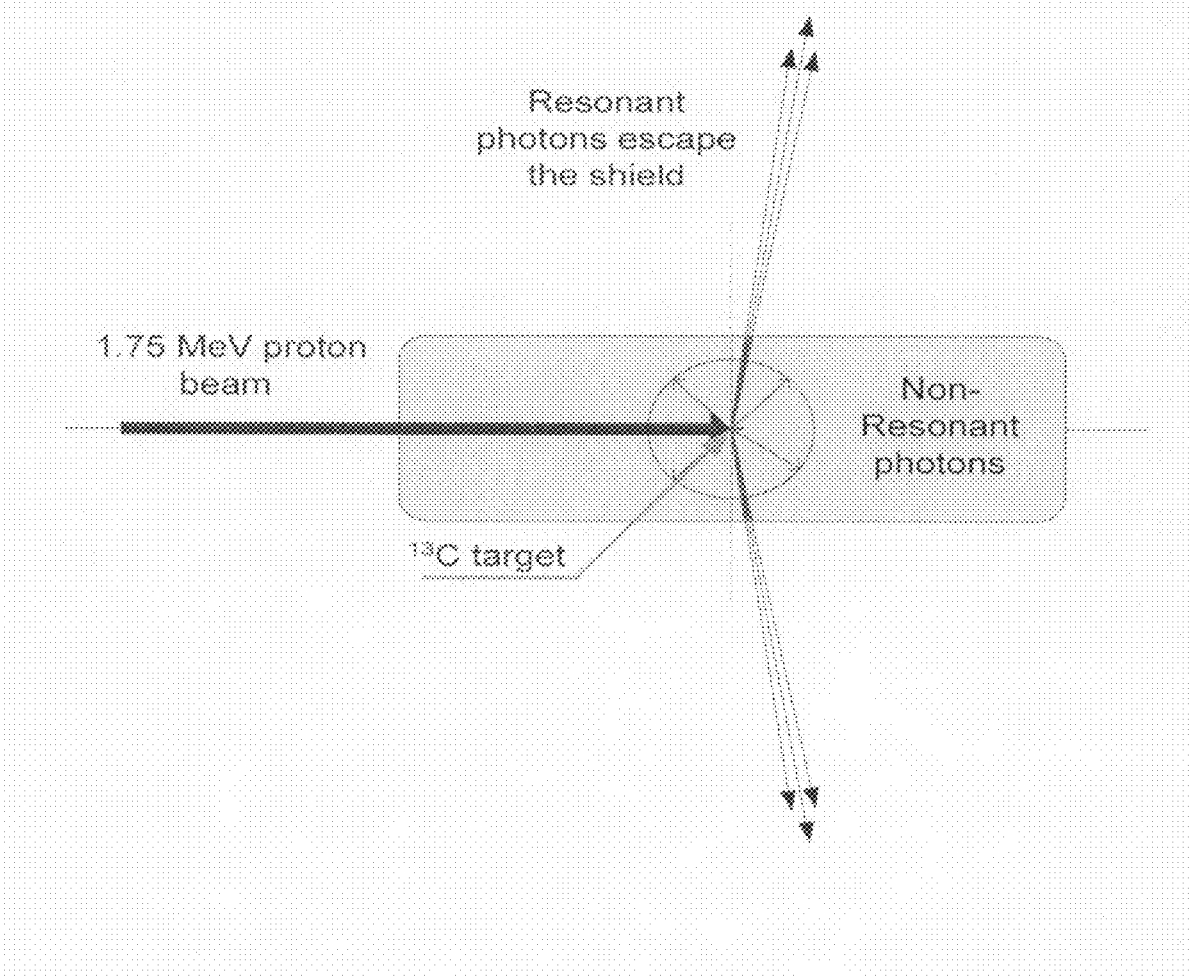
FIG. 2 is a schematic of a proton target for production of resonant photons.

The accelerator system described herein employs a high current negative ion source, a tandem accelerator and high voltage power supply that will deliver beam current of 10 mA or more of protons or deuterons at energies up to 3 MeV or higher to appropriate targets to produce intense beams of penetrating high energy neutrons or photons. The resultant radiation beams together with appropriate detectors and computers to analyze and present results form the complete active interrogation and detection system.

Three methods are available to detect the various threats (see FIG. 1). The first method involves the use of nuclear resonance absorption to detect nitrogen based chemical explosives (NCE) and shielded dirty bombs, the second method involves the use of delayed fission to detect fissionable special nuclear materials (SNM) and shielded dirty bombs, and the third method involves the simple absorption of high energy neutrons to detect SNM.

The first threat of nitrogen-based chemical explosives (NCE) may be detected by the resonant absorption of gamma rays in nitrogen. The resonance at 9.17 MeV is very narrow (150 eV) so the energy width of the gamma rays that will be absorbed is limited to this range. Gamma rays with energy of 9.17 MeV are very penetrating and so they can also be used to "look for" shielded dirty bombs as well as NCE.

One problem addressed by the present invention is how to produce gamma rays with this precise energy. Gammas with energy 9.17 MeV and width of 150 eV can be produced by the reaction of 1.75 MeV photons on $^{13}$C to produce $^{14}$N in an excited state. More particularly, the portion of the excited $^{14}$N (approximately 5%) which decays to the nitrogen ground state emits a resonant gamma photon with the required energy. Due to recoil effects, only the photons emitted at an angle of 81°±1.5° have the energy needed to be absorbed again. All these constraints on the photon energy lead to strong constraints on the proton beam dimensions, divergence and energy spread at the reaction target. Previous efforts to produce these conditions have failed. The design of the present invention incorporates and satisfies all these constraints including the requirement that the photon flux, which is proportional to the proton current, is high enough to detect the quantities of explosive that would be dangerous if concealed in a truck or cargo container.

The high energy photons produced in the $^{13}$C(p,γ)$^{14}$N reaction have sufficiently high energy to penetrate into packed cargo containers and the re-emitted gamma rays have enough energy to exit the container and be detected. If the incident photons are not transmitted to the detectors opposite the source, they have either encountered a high density material that is a shield for a dirty bomb, or they have intercepted a quantity of nitrogenous material that may be a chemical explosive. The nature of the threat can be determined by comparing the transmission of the resonant and non-resonant photons (i.e. those emitted at the specified angle of 81° with the transmission of those emitted at another angle (such as 90°).

The same accelerator and target system used to generate resonant photons for detection of chemical explosives and dirty bombs can be configured to produce high energy neutrons and protons which can be employed to detect SNM or shielded dirty bombs. Special nuclear materials will fission when the fissile materials absorb neutrons or due to photofission induced by photons with energy greater than about 5 MeV. Delayed emission of fission neutrons and high energy photons are a uniquely and unambiguously indication of the presence of SNM. While fission neutrons are low energy and may not escape to reach the detectors that are located outside the container, the high energy photons that are emitted after fission are 10 times more intense than the neutrons, as well as more penetrating, and thus are more able to reach the detectors. If high energy neutrons are the interrogating beam and the contents of the container are low density hydrogenous materials, the neutrons will be slowed down and absorbed before they reach the SNM in which case they will not detect its presence. If the contents are high density, the neutrons will scatter without significant loss of energy. The signal produced by delayed fission depends on the path length and density of material between the neutron source and the SNM and from the SNM to the detectors. A high density material will pass neutrons but it will reduce the intensity of photons at the SNM. A low density material will pass high energy photons but it will greatly attenuate a neutron beam. If the bulk content of the cargo being scanned is not well documented, it would be best to have a mixed high energy neutron and photon interrogating source. The system of the present invention has the ability to generate a mixed neutron and photon beam to detect the SNM.

The third threat of shielded "dirty" bombs can be detected by measuring the attenuation of the high energy gamma rays used to induce fission or the resonant high energy gammas used to detect chemical explosives. In other words, the same high energy gammas produced in either fluorine of $^{13}$C targets can be used to detect the high density shield needed to disguise a dirty bomb.

To overcome the limitations associated with prior art systems and methods, the system described herein incorporates a high brightness surface plasma negative ion source and a unique type of tandem accelerator. The negative ion source is a surface plasma source (SPS). The SPS is based on the principle of cesium catalysis of negative ion formation. The ion source employs a thin monolayer of cesium on the surface of the cathode to enhance negative ion production and it incorporates electrode materials and geometry to maintain preferred temperatures on critical surfaces. The cathode to anode electrode spacing is kept as small as possible to reduce negative ion destruction. The source can be operated in pulsed mode up to 1 kHz repetition rate by use of a pulsed gas valve that modulates the pressure of gas in the plasma region. This type of ion source produces a very stable ion beam with small diameter, high current and relatively low energy spread and angular divergence.

The tandem accelerator employs a nested coaxial array of vacuum insulated electrodes through which the ion beam traverses radially. The high voltage power supply is an industrial grade stabilized voltage multiplier type such as the magnetically coupled ELV manufactured in Novosibirsk, Russia or the capacitive coupled Dynamitron manufactured by Radiation Dynamics in the U.S.A. or the Cockroft-Walton type manufactured by Nissin High Voltage in Japan).

The energetic proton or deuteron ion beams generated by this combination of high brightness ion source and high transmission tandem ion accelerator system has high current, low emittance and high energy resolution and stability which results in an intense source of resonant or non-resonant photons or high energy neutrons when it interacts with an appropriate target.

One method of detecting nitrogen explosives inside a container utilizes gamma resonance fluorescence (GRF). Typically, this method employs high energy (9.17 MeV) photons to resonantly induce a response from the nitrogen in the explosive. The resonant response is detected with appropriate sensors indicating the presence of nitrogen. See, e.g., U.S. Pat. Nos. 5,420,905, 4,941,162, 5,247,177 and 5,040,200.

The method of nitrogen detection is based upon resonant absorption of photons or gamma rays. The resonant photon energy required is 9.17 MeV. The width of the resonant energy level is 122 eV. Production of photons with this energy and within this energy width can be accomplished by proton absorption in carbon-13 isotope at incident proton energy of 1.75 MeV. At this energy, the incident proton is resonantly absorbed in the carbon nucleus producing nitrogen-14 in an excited state. The excited nitrogen nucleus decays either back to the original $^{13}$C+p (95%) or it gamma decays to the ground state of $^{14}$N, giving off a 9.17 MeV photon.

Those skilled in the art of nuclear physics will know that gamma rays emitted from the excited state of the $^{14}$N nucleus cannot be resonantly reabsorbed in another $^{14}$N nucleus because the Doppler shift due to recoil of the first nitrogen nucleus reduces the gamma ray energy to a value outside the width of the 9.17 MeV energy level. However, when the $^{14}$N excited state is produced in the nuclear reaction,

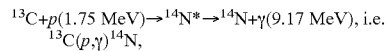

$^{13}$C+p(1.75 MeV)→$^{14}$N*→$^{14}$N+γ(9.17 MeV), i.e. $^{13}$C(p,γ)$^{14}$N, with 1.75 MeV protons, the center of mass motion of the initial state adds enough energy so that photons emitted in a ±1.5° angular interval at the angle 80.7° with respect to the incident proton have the correct energy to be resonantly reabsorbed in nitrogen. The method of gamma resonant absorption (GRA) or gamma resonant fluorescence (GRF) or nuclear resonant absorption (NRA) for detection of nitrogen explosives depends, therefore, very strongly on the angle of emission of the photons relative to the incident protons. The strong correlation between energy and angle of the photons emitted from the excited nitrogen nucleus together with the very narrow energy width of the nitrogen resonance leads to very stringent requirements on the shape, size, divergence and energy spread of the proton beam at the point of contact with the $^{13}$C target. The angle 80.7°±1.5° will hereinafter be denoted as 81°.)

In order to achieve these constraints on photon angle and energy of photons emitted at the first target, it is necessary to assure that the diameter and angular divergence of the ion beam at the first target is within specified limits. That is, the angular divergence should be ±1.5° and the beam diameter should be as small as possible.

The connection between the beam diameter and beam divergence is determined by a fundamental property of the beam named the beam emittance, also known as the phase space area. The emittance of an ion beam is a quantity that cannot be changed once the beam is formed, provided the electric forces that govern the transport and acceleration of the beam act through conservative forces. Because of this rule, the problem of achieving ideal conditions at the target end of an accelerator depends very strongly on optimizing the ion beam at the its source. Also, care must be exercised during acceleration and transport of the beam to the target so that the phase space area stays organized as much as possible into a simple connected shape.

Referring to FIG. 2, the negative ion beam from the SPS source is injected into the vacuum insulated tandem accelerator where it is accelerated, stripped of two electrons and accelerated again to ground potential. There is it made to impact a $^{13}$C target where the resonant photons are produced.

A collimator made of an absorber material (steel, lead, tungsten or concrete in the case of gamma rays) is positioned with its center coincident with the geometrical center of the source of radiation (i.e. the point where the ion beam strikes the target). With a point source and a collimator having a slot at 81°, the emerging photons would all have the resonant energy, 9.17 MeV. However, even a small angular divergence of the incident protons results in a spreading out of the energy spectrum of photons that pass through the collimator. This contaminated photon energy spectrum reduces the sensitivity of the detection method. Thus, it is preferred to have an angular divergence within definite limits to optimize the sensitivity of the method. The ion source/accelerator system described in this patent provides a method to produce an ion beam with the current, divergence, energy stability and resolution to optimize this method of detection.

Accordingly, in one aspect, the invention provides a system for detection of explosives and SNM comprising a negative hydrogen ion source and tandem accelerator for generating a high energy low emittance beam of protons. The source of ions is a surface plasma negative source that employs cesium to catalyze the negative ion production. The ion source comprises a series of electrodes and gaps arranged in a specific way to maximize the production of negative ions on the surface of the electrodes and minimize their destruction after they are produced. The ion source electrodes are made in a particular shape to provide a circular (pencil) or ribbon like (slit) beam of negative ions. The electrodes and insulating materials of the ion source are chosen to provide specific potentials and thermal and electrical resistance to maintain the gas discharge and temperatures needed for stable and long lived operation.

It is important to note that a very stable plasma discharge in the ion source is required to optimize the beam emittance. Fluctuations and instabilities in the ion source plasma add to the time averaged phase space of the ion beam.

The phase space of the ion beam is critical in two specific locations along the beam axis. One is at the location in the mid-point of acceleration in the tandem where the high current beam is confined to pass through a narrow tube called the stripper canal. The canal is made long in length and small in diameter to provide high resistance to gas flow. The gas pressure and length of the stripper canal are chosen to optimize removal of electrons from the negative ion beam so the beam that emerges is primarily positive ions. The canal may have baffles to enhance the gas pressure inside the canal while maintaining a high vacuum in the space outside. The geometrical constraint on the gas pressure and gas flow places a corresponding constraint on the beam size and divergence (i.e. the beam emittance at the stripper canal). The second critical location where the phase space is critical is at the photon generating target. As discussed above, for the resonant $^{13}$C(p,γ)$^{14}$N reaction, the phase space of the beam at the target directly determines the angle of emission of the photons that can be resonantly reabsorbed in nitrogen based explosive. This angle is very small and is fixed relative to the proton beam axis and the Z-axis location where the proton beam energy is at the resonant energy for absorption (1.75 MeV).

Certain versions of the SPS source produce beam current in the range from 5 mA to 25 mA DC and up to 100 mA pulsed current. With placement of magnets at the exit of the ion source, parasitic electrons are swept out of the negative ion beam before acceleration. Electrostatic elements are used to prevent back streaming positive ions from sputtering and destroying the negatively charged electrodes of the ion source. A mono-layer of Cs on specific electrodes acts as catalyst to assure stable, steady operation of the ion source adding to the low emittance and high current capability.

Because the binding energy of an electron on a hydrogen atom is extremely small (less than 1 eV), the electron is easily detached resulting in a neutral hydrogen atom. The loss of negative ions due to detachment is related to the path length traveled by the ions.

Figure 3:
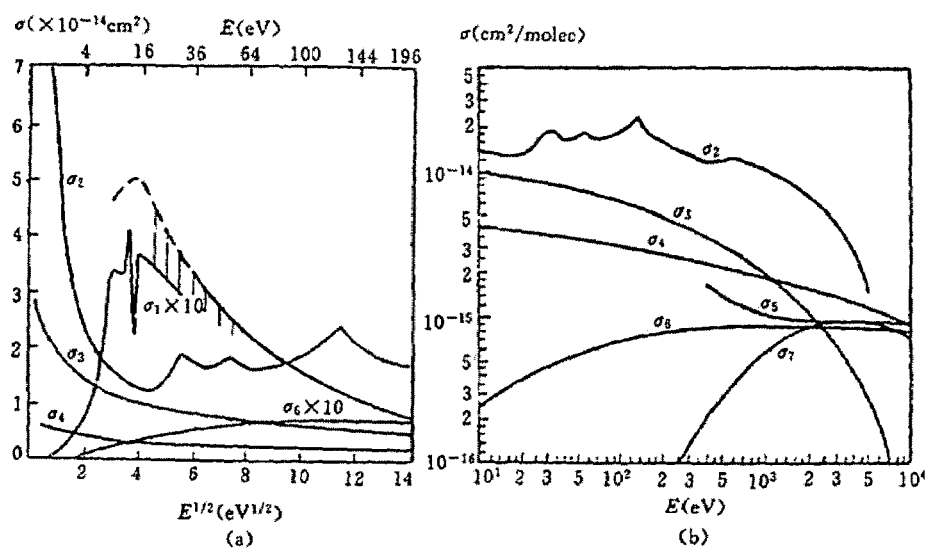
FIG. 3 shows the cross-sections of negative ion destructions in collisions with plasma particles.

In particular, when the negative biased emitter is bombarded by the ions in the plasma, a flux of NI is produced. If $j^+$ is the positive ion flux in the plasma and j is the flux of secondary NI emitted by the cathode, $$j^- = Kj^+ = Kn_p v, \quad (1)$$

where $n_p$ is the plasma density, v is an ion velocity related to the plasma temperature and K is the secondary emission coefficient. As the negative ions move toward the anode, their flux decreases according to the relation, $$j^-(x) = Kj^+ \exp\left[-\int_0^d n_e\left(\left(\frac{\sigma_1 v_e}{v^-}\right) + \sigma_2\right)dx - \int_0^l n_g \sigma_6 dx\right], \quad (2)$$

where d is the thickness of the plasma layer, l is the emitter-anode gap, and the $v_q$'s are cross sections for NI destruction in collisions with various particles (examples of these cross sections are presented in FIG. 3), $v_e$ is plasma electron velocity, $v^-$ is negative ion velocity, $n_e$ is electron density, $n_g$ is gas density. Substituting Eq. (1) into Eq. (2) gives $$j^-(x) = (Kn_p v^+) \exp\left[-\int_0^d n_e\left(\left(\frac{\sigma_1 v_e}{v^-}\right) + \sigma_2\right)dx - \int_0^l n_g \sigma_6 dx\right]. \quad (3)$$

The loss can be suppressed by reducing the path length.

The ion beam from a Surface Plasma Negative Ion Source has a very high current density (j~1-3 A/cm$^2$) and large perveance. For transport of beam with this high current density, it is necessary to use strong space charge neutralization or very strong continuous focusing by electrostatic forces similar to that done in the radiofrequency quadrupole accelerator (RFQ), a Low Energy Beam Transport (LEBT) with electrostatic electrostatic quadrupole. Another way to reduce destruction of negative ions in regions that are free from electrostatic forces is to generate an electron rich plasma in the path of the in beam. This produces resonant attachment of electrons and thereby inhibits the effective detachment process. The electron rich plasma can be produced by a highly efficient hollow cathode discharge ion source.

Electrostatic ion accelerators that operate at voltages above a few hundred kilovolts typically employ a voltage graded vacuum enclosure called the acceleration tube through which the ions or electrons pass during acceleration. Typical acceleration tubes are comprised of a vacuum tight axially symmetric array of metal electrodes separated by insulators that are usually made of epoxy, ceramic or glass. Voltage applied at the ends of the acceleration tube is graded and controlled by electrical resistors or corona discharge points arranged in series and attached to the individual electrodes. Those skilled in the art know that electrical charge can accumulate on the insulator and cause ion beam instability or discharge of voltage between electrodes. This behavior acts to limit the current that can be transported through the acceleration tube. In some designs, the metal electrodes in the interior (vacuum side) of the acceleration tube are shaped to shield the insulators from the ions or electrons in the particle beam. This improves the transmission capability but the shape of the shields causes a gas trap that increases vacuum pressure and finally limits the beam current or results in voltage break down of the acceleration tube.

Figure 4:
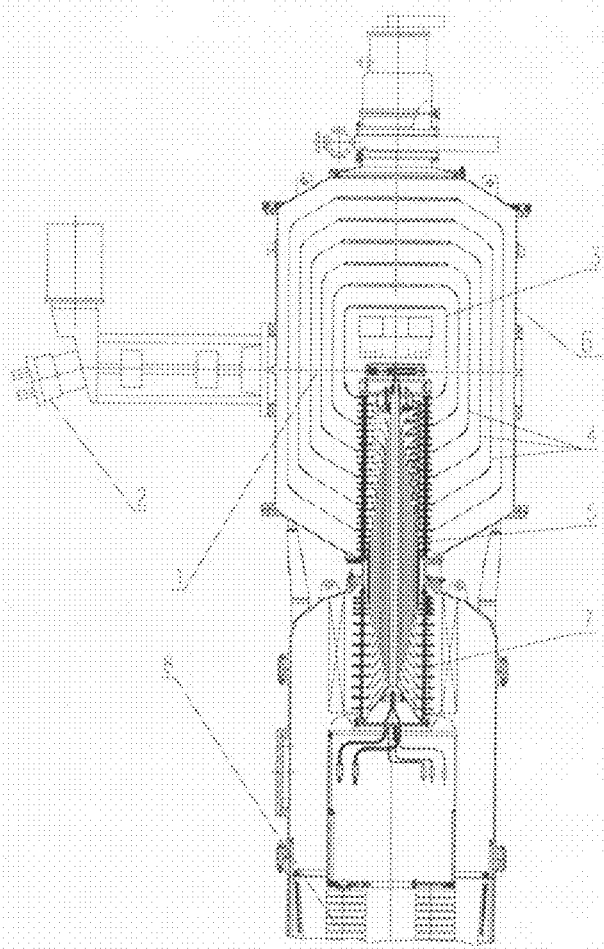
FIG. 4 is a schematic showing the major components of the vacuum insulted tandem accelerator.

Accordingly, the electrostatic tandem accelerator of this invention, i.e., accelerator 10 of FIG. 4, provides a configuration in which there is no acceleration tube. The tandem accelerator consists of a DC high voltage power supply situated in a vessel pressurized with high pressure insulating gas. The high voltage power supply can be a capacitance coupled voltage multiplier circuit such as the series coupled Cockroft-Walton or parallel coupled Dynamitron accelerators or it can be inductively coupled such as the parallel driven ELV or the series driven inductive type designed by High Voltage Engineering and TRIUMF.

The output of the high voltage power supply is electrically connected to the stripper canal, which is located in a separate vacuum enclosure. The electrical connection can be made via a cable connection or it can be made through a pair of gas insulated tubes that contain a voltage insulating gas, liquid or solid material through which the conductor passes. The voltage gradient from the high voltage terminal to ground in the pressure vessel and from ground to the stripper canal located in the high voltage terminal of the tandem vacuum vessel is controlled using an array of metal electrodes separated by insulators just as was described above for the accelerator beam tube. However, instead of vacuum, the connecting tubes are filled on the inside with insulating gas, liquid or solid. The gradient along the tube is established by means of a resistor divider that attaches to the metal electrodes.

Those skilled in the art know that in operation of a classical tandem accelerator, a negative ion beam is injected into the tandem acceleration tube at ground potential. The negative ions are accelerated in the electric field that exists in the acceleration tube. The ions gain energy corresponding to the potential difference between ground potential, where the beam is injected, to the potential of the stripper canal. According to standard practice, the stripper canal contains a gas maintained at a specific pressure that together with its overall length provides enough collisions to remove two electrons from the injected ion beam. The positive ions exit from the stripper and are accelerated back to ground in the tandem vacuum.

This invention provides a tandem accelerator vessel that has no acceleration tube. Instead, it is comprised of a nested array of coaxial cylindrical electrodes to uniformly divide the voltage from the potential of the stripper canal to ground potential. Each cylindrical electrode contains a pair of apertures cut into the electrodes along a line of sight that passes through the stripper canal. The negative ions are injected into the tandem vacuum vessel and are accelerated by the potential difference between successive apertures up to the stripper canal. After being stripped of their electrons in the stripper canal, the generated positive ions are accelerated to ground through the diagonally opposed apertures. The potential difference between adjacent cylinders is chosen to be between 200 kV and 300 kV to prevent voltage breakdown and maintain a compact assembly. The apertures may be circular or non-circular to accommodate a ribbon beam and provide better optics and higher beam current. To optimize high current transmission, the apertures may be extended in the axial (Z) direction in a non-symmetrical configuration to provide electrostatic quadrupole focusing.

The vacuum insulated tandem accelerator eliminates the two problems of runaway vacuum and voltage breakdown by eliminating the beam tube. The vacuum vessel that contains the stripper and coaxial nested array of cylindrical electrodes is continuously pumped by a high speed high vacuum pump to a high vacuum on the order of $10^{-6}$ Torr to maintain good beam transmission and reduce loss of current due to scattering. This approach provides control of beam phase space throughout the acceleration process.

After acceleration in the tandem accelerator, the 1.75 MeV proton beam is transported to the $^{13}C$ target using standard techniques to separate out neutral hydrogen atoms. Classical feedback techniques can be used to maintain the voltage at the resonant energy to within ±0.1%.

The high current low emittance ion beam will produce resonant and non-resonant photons when it impacts the $^{13}C$ target. For the particular surface plasma type negative ion source described above, the ion current can be dc or pulsed. Due to the particular design of this surface plasma ion source, the range of current is variable from 5 mA to 25 mA in dc operation and up to 100 mA in pulsed mode. This corresponds to a power level of about 10 kW to about 50 kW dc and instantaneous power of about 175 kW in pulsed mode.

The dimension and divergence of the generated proton beam at the target will be in the range defined by the geometry of the collimator and the emittance of the ion beam. The $^{13}C$ target thickness is chosen to correspond to an energy loss not more than two times the energy spread in the ion beam. For example, with a 1% energy spread in the proton beam, the target thickness in energy units is less than 3.5 keV. The power dissipation in the target will be in the same percentage as the energy dissipation. That is, the power dissipation in the $^{13}C$ target ranges from 17.5 W at 5 mA to 175 W at 50 mA. The average power dissipated in the pulsed beam case depends on the duty cycle of the pulsed beam. The power density depends on the area of the proton beam on the target. The spot size of about 2 cm can be achieved with the ion beam generated in the manner described here. The resultant power density can be handled by radiant heat transfer the surrounding cooled surfaces.

Figure 5:
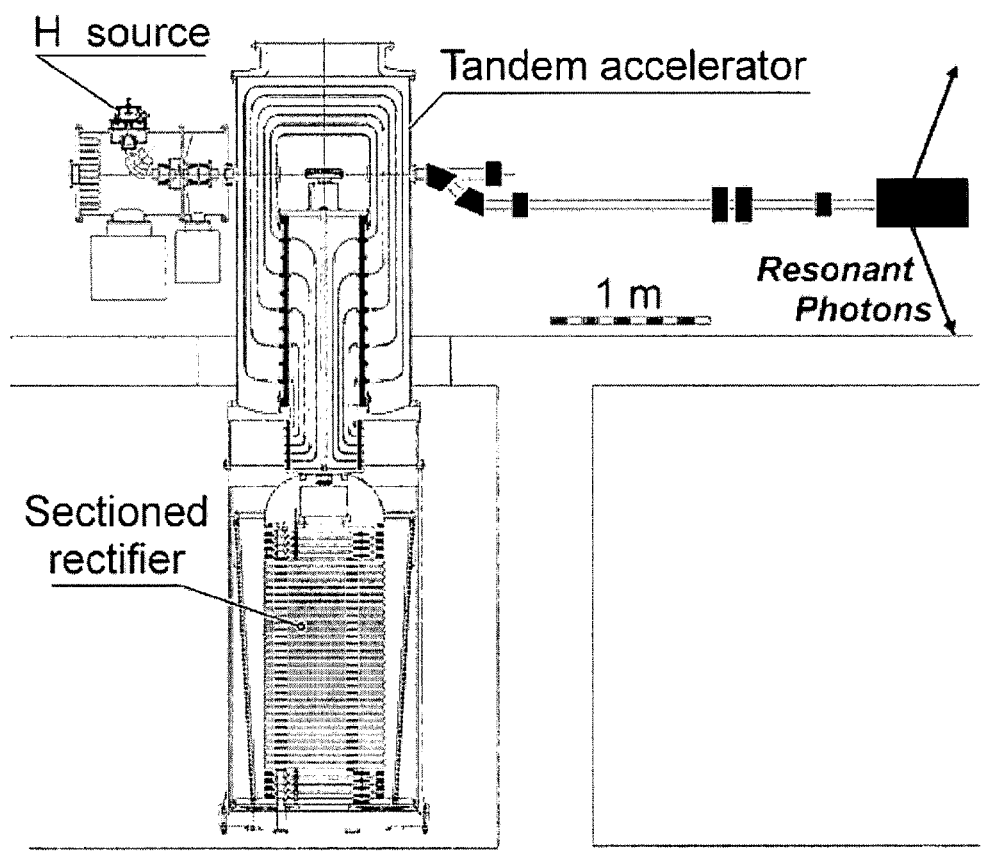
FIG. 5 is an illustration of a preferred embodiment of an ion source, vacuum insulated tandem accelerator and resonant photons target system.

FIG. 5 shows a preferred embodiment of the system for detection of explosives and weapons usable nuclear material. The system is comprised of a high current surface plasma negative hydrogen ion source, a low energy beam transport system, a vacuum insulated tandem accelerator, a high energy beam transport system and a target to generate high energy photons from a specific nuclear reaction. Additional elements not shown in the figure are control and safety systems for protection of equipment and personnel; vacuum pumping equipment to maintain high vacuum in the tandem tank, the high energy and low energy beam transport systems and in the region near the target; and a system for transferring high pressure ($SF_6$) insulating gas from storage containers into the high voltage power supply.

The ion source produces a high brightness beam of negative hydrogen ions by direct extraction from a surface plasma ion source. The negative ions are extracted from the ion source, accelerated to about 25 keV to 50 keV beam, focused and passed through a bending magnet to separate electrons and other ions that may be produced in the source. In the low energy beam transport (LEBT) system, strong space charge neutralization is employed to prevent beam expansion due to Coulomb repulsion in the high current low emittance ion beam. The preferred method of space charge neutralization is through production of a dense plasma of ions and electrons to provide charge neutralization ion the immediate vicinity of the ion beam.

In addition to the control of beam spot size, beam divergence, and beam current, it is very important to control the energy of the ion beam incident on the target. Variation in beam energy is typically measured by use of a magnetic energy analyzer or other means such as measuring the yield of resonant photons from specific nuclear reaction.

There are two important contributions to beam energy variations. One is the change of ion beam energy due to slow drift due in the setting of components that control the energy of the accelerator. The second are faster variations due to ripple voltage. Energy variation due to ripple voltage is made worse when the beam current is high, which is the case in this application where the current is 5 mA or greater. Slow or "long term" drift in ion beam energy is usually controlled by standard feedback techniques in which a compensating signal is applied to the accelerator energy control system. This invention concerns the cancellation of the short term drift due to ripple voltage when the current is high. The fast energy fluctuations are difficult to control by adjusting accelerator parameters because of the slow response function of most high energy accelerators. In this invention, fast ion beam energy fluctuations, such as those related to the high current beam, are compensated by a magnetic induction coil that produces a local electric field to accelerate the ion beam directly. The induction coil would be located at the exit of the accelerator and before the entrance to the magnetic energy filter or other device used to sense the variation in the beam energy.

Figure 6:
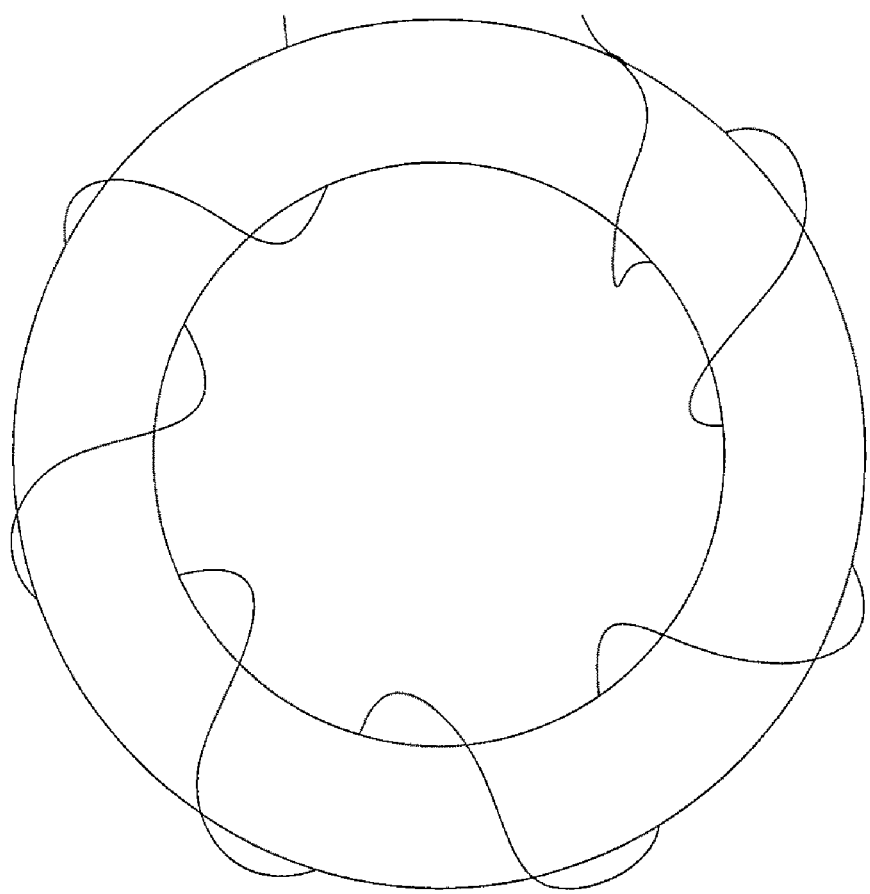
FIG. 6 shows a magnetic induction coil used to control energy fluctuations in the accelerated beam.

The magnetic induction coil 10 is wound in the form of a torus (see FIG. 6), a method that generates an azimuthal magnetic field. The changing azimuthal magnetic field generates a perpendicular electric field along the axis of the torus. The strength of the electric field is proportional to the rate of change of the magnetic field. The equations that govern the process are the Maxwell Equations. In particular, written in integral from, the equations $$\oint \vec{E} \cdot \vec{dl} = -\partial/\partial t \int_S \vec{B} \cdot \vec{dS}, \quad (1.1)$$

and $$\oint \vec{H} \cdot \vec{dl} = \int_S \vec{i} \cdot \vec{dS} + \frac{\partial}{\partial t}\int_S \vec{D} \cdot \vec{dS}, \quad (1.2)$$

where $\vec{E}, \vec{D}, \vec{B}, \vec{H}$, are the usual electromagnetic field vectors and i is the current density. Integrating (1.2) gives for the magnetic field, $$B(t)=\mu N I_0 e^{j\Omega t}/(2\pi R), \quad (1.3)$$

where we have used $\vec{B}=\mu\vec{H}$, $R=(b+a)/2$ is the mean radius of the torus with outer radius b and inner radius a, and NI is the number of Ampere turns. Inserting this expression into Eq. (1.1) gives the change of energy $e\Delta V$ of an ion of charge, e, that passes through the center of the torus, $$\oint e\vec{E} \cdot \vec{dl} = \Delta eV = -j\omega \times e \frac{\mu NI}{[2\pi(b+a)/2]}\pi(b-a)^2, \quad (1.4)$$

where we have used $I(t)=I_0 e^{j\omega t}$. This method of energy compensation acts directly on the ion beam after it exits the accelerator and can be used to hold the beam energy on the correct energy to maximize the output flux of the resonant photons. In Eq. (1.4), $\omega=2\pi f$ is the angular frequency of the energy ripple.

It will be appreciated that the present invention has been described herein with reference to certain preferred or exemplary embodiments. The preferred or exemplary embodiments described herein may be modified, changed, added to or deviated from without departing from the intent, spirit and scope of the present invention, and it is intended that all such additions, modifications, amendment and/or deviations be included within the scope of the following claims.

What is claimed is:

1. An active interrogation and detection system for detecting dangerous materials concealed within a container, comprising:
    a high current negative ion source for providing a charged-particle beam;
    a high current tandem accelerator having an entrance and an exit, said accelerator receiving said charged-particle beam through said entrance and accelerating said charged-particle beam to a pre-selected level to provide an accelerated beam at said exit;
    a target material located outside of said accelerator and in the pathway of said accelerated beam exiting said accelerator whereupon impact of said accelerated beam with said target material produces a penetrating beam for direction into said container;
    at least one detector located proximate said container for detecting a pre-identified signal provided by the interaction of said penetrating beam and said dangerous materials concealed within said container; and
    an induction coil located proximate said exit of said accelerator for controlling energy fluctuations in said accelerated beam.

2. The system according to claim 1, wherein said induction coil produces a local electric field located to act directly upon said accelerated beam.

3. The system according to claim 2, wherein said induction coil is wound in the form of a torus.

4. The system according to claim 3, wherein said induction coil generates an azimuthal magnetic field.

5. The system according to claim 4, wherein said azimuthal magnetic field generates a perpendicular electric field along the axis of said torus.

6. The system according to claim 5, wherein said accelerated beam passes through said torus.

7. The system according to claim 6, further comprising a magnetic energy analyzer located along said pathway between said exit of said accelerator and said target, and wherein said induction coil is located between said exit and said analyzer.

8. The system according to claim 7, wherein said induction coil is formed of a plurality of tori.

9. The system according to claim 8, wherein said dangerous materials are selected from the group consisting of special nuclear materials, radiological materials and chemical explosives.

\* \* \* \* \*

UNITED STATES PATENT AND TRADEMARK OFFICE
CERTIFICATE OF CORRECTION

| | |
|---|---|
| PATENT NO. | : 7,501,624 B1 |
| APPLICATION NO. | : 11/811539 |
| DATED | : March 10, 2009 |
| INVENTOR(S) | : Farrell et al. |

It is certified that error appears in the above-identified patent and that said Letters Patent is hereby corrected as shown below:

On the Title Pg Item (63)

Please add: --Related U.S. Application Data Continuation of application No. 11/414,769, filed on April 28, 2006, which claims the benefit of provisional application No. 60/676,090, filed on April 28, 2005.--

Column 8, line 14

Now reads: "and j is the flux of"

Should read: --and $\bar{j}$ is the flux of--

Column 8, line 30

Now reads: "$v_q$'s"

Should read: --$\sigma_q$'s--

Column 11, line 50

Now reads: "where $\overline{E}, \overline{D}, \overline{B}, \overline{H},$"

Should read: --where $\vec{E}, \vec{D}, \vec{B}, \vec{H},$ --

UNITED STATES PATENT AND TRADEMARK OFFICE
CERTIFICATE OF CORRECTION

PATENT NO. : 7,501,624 B1
APPLICATION NO. : 11/811539
DATED : March 10, 2009
INVENTOR(S) : Farrell et al.

It is certified that error appears in the above-identified patent and that said Letters Patent is hereby corrected as shown below:

Column 18, line 27

Now reads: "$B(t) = \mu N I_0 e^{j\Omega t}/(2\pi R)$,"

Should read: --$B(t) = \mu N I_0 e^{j\omega t}/(2\pi R)$--

Signed and Sealed this

Eighth Day of September, 2009

David J. Kappos
*Director of the United States Patent and Trademark Office*